United States Patent
Ravindran

(10) Patent No.: US 11,054,279 B2
(45) Date of Patent: Jul. 6, 2021

(54) ADAPTIVE STEP DETECTION

(71) Applicant: Texas Instruments Incorporated, Dallas, TX (US)

(72) Inventor: Sourabh Ravindran, Dallas, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 1347 days.

(21) Appl. No.: 13/745,714

(22) Filed: Jan. 18, 2013

(65) Prior Publication Data
US 2013/0191069 A1    Jul. 25, 2013

Related U.S. Application Data

(60) Provisional application No. 61/588,388, filed on Jan. 19, 2012.

(51) Int. Cl.
| | | |
|---|---|---|
| G01C 22/00 | (2006.01) | |
| G06F 1/16 | (2006.01) | |
| A61B 5/11 | (2006.01) | |

(52) U.S. Cl.
CPC ......... *G01C 22/006* (2013.01); *G06F 1/163* (2013.01); *G06F 1/1694* (2013.01); *A61B 5/1123* (2013.01)

(58) Field of Classification Search
USPC ...................................................... 702/160
See application file for complete search history.

(56) References Cited

U.S. PATENT DOCUMENTS

| | | | | |
|---|---|---|---|---|
| 6,298,314 | B1* | 10/2001 | Blackadar et al. | 702/178 |
| 7,877,226 | B2* | 1/2011 | Chan et al. | 702/160 |
| 8,801,637 | B2* | 8/2014 | Nishibayashi | 600/595 |
| 2007/0143068 | A1* | 6/2007 | Pasolini et al. | 702/160 |
| 2009/0058636 | A1* | 3/2009 | Gaskill et al. | 340/539.11 |
| 2009/0163835 | A1* | 6/2009 | Logan et al. | 600/595 |
| 2009/0221403 | A1* | 9/2009 | Chan et al. | 482/8 |
| 2010/0010774 | A1* | 1/2010 | Ma et al. | 702/160 |
| 2011/0131005 | A1* | 6/2011 | Ueshima et al. | 702/141 |
| 2013/0053990 | A1* | 2/2013 | Ackland | 700/91 |
| 2013/0080255 | A1* | 3/2013 | Li et al. | 705/14.58 |
| 2013/0085700 | A1* | 4/2013 | Modi et al. | 702/104 |
| 2013/0090881 | A1* | 4/2013 | Janardhanan et al. | 702/104 |

* cited by examiner

*Primary Examiner* — Paul D Lee
(74) *Attorney, Agent, or Firm* — Ebby Abraham; Charles A. Brill; Frank D. Cimino

(57) ABSTRACT

A pedometer with a three-axis accelerometer provides reliable step counts while worn on the wrist. Three-axis accelerometer data is combined into a single combined data stream. Each positive slope region around an inflection point in the combined data stream that has positive slope, a magnitude that exceeds an amplitude threshold value and that spans a time period that exceeds a time threshold value is identified. Each negative slope region around an inflection point in the combined data stream that has negative slope, a magnitude that exceeds an amplitude threshold value and that spans a time period that exceeds a time threshold value is identified. A step count is incremented for each occurrence of an identified positive slope region that is separated by an identified negative slope region as a step.

11 Claims, 7 Drawing Sheets

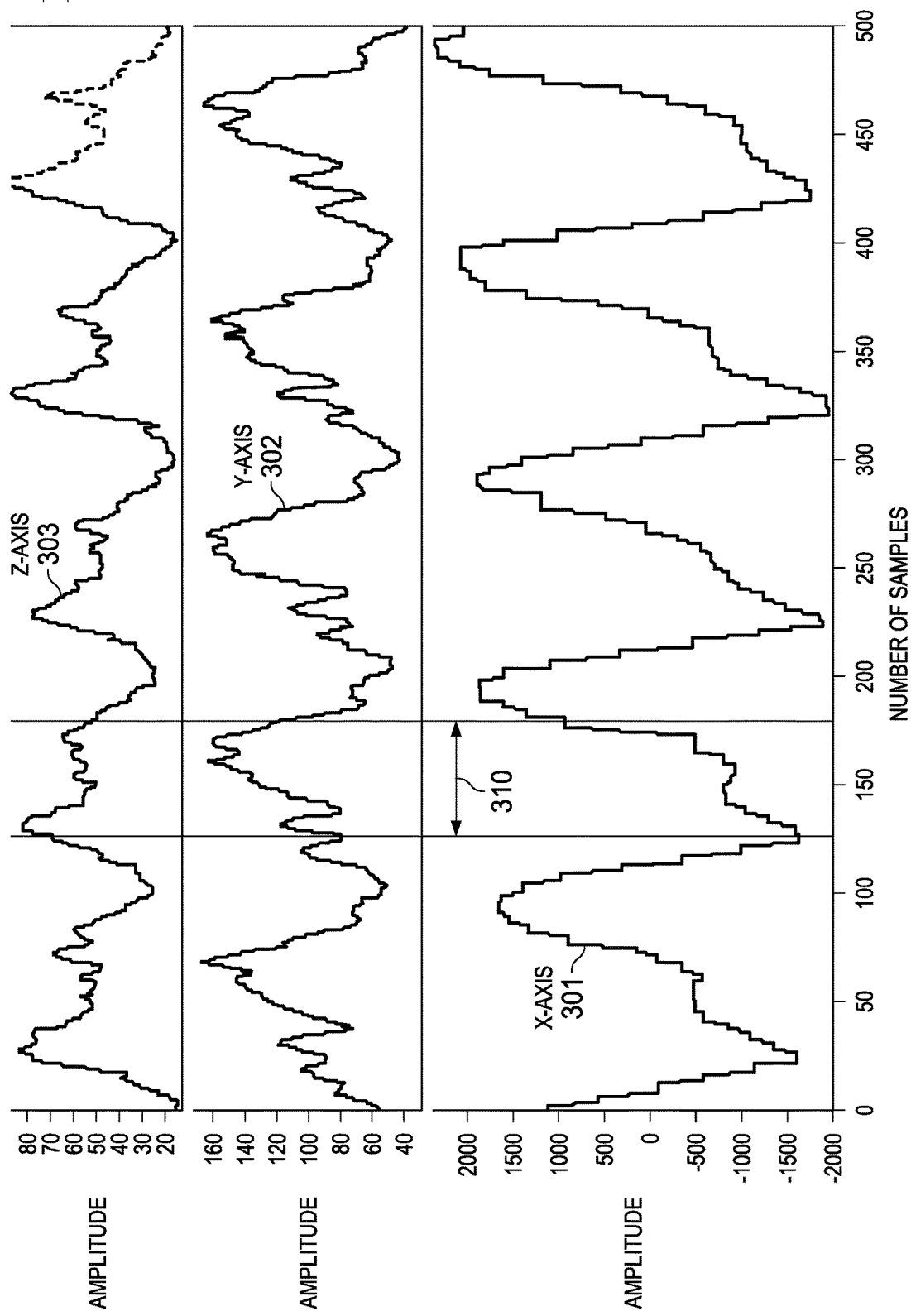

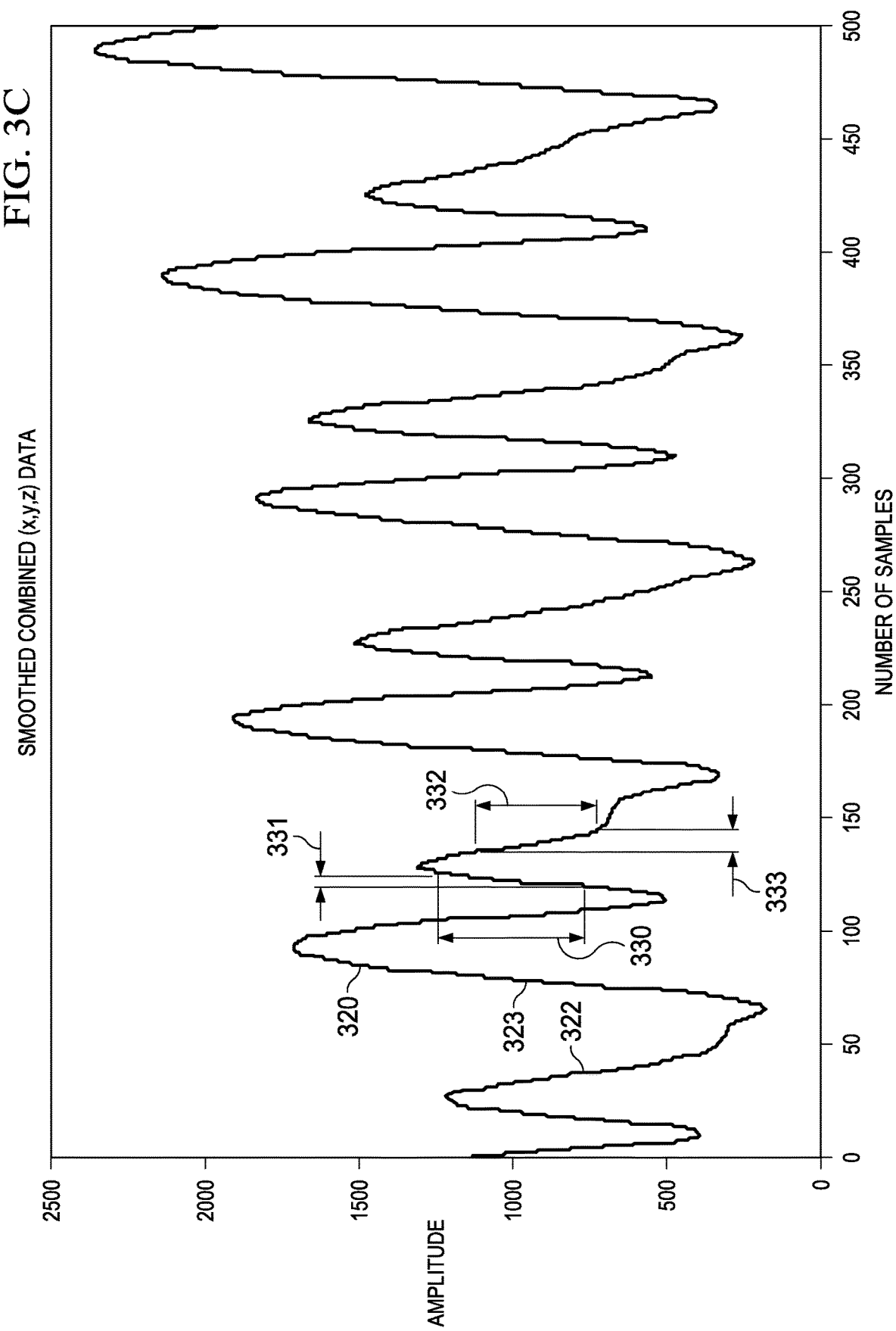

ADAPTIVE STEP DETECTION

CLAIM OF PRIORITY UNDER 35 U.S.C. 119(e)

The present application claims priority to and incorporates by reference U.S. Provisional Patent Application No. 61/588,388, filed Jan. 19, 2012, entitled "Method and Apparatus for Low-Complexity Pedometer Using A 3-Axis Accelerometer".

FIELD OF THE INVENTION

Embodiments of the invention generally relate to pedometers, and in particular to pedometers that can be worn on the wrist as well as on the torso.

BACKGROUND

A pedometer is a device, usually portable and electronic or electromechanical, that counts each step a person takes by detecting the motion of the person's hips. Because the distance of each person's step varies, an informal calibration, performed by the user, may be required if presentation of the distance covered in a unit of length (such as in kilometers or miles) is desired, though there are now pedometers that use electronics and software to automatically determine how a person's step varies.

Used originally by sports and physical fitness enthusiasts, pedometers are now becoming popular as an everyday exercise measurer and motivator. Often worn on the belt and kept on all day, it can record how many steps the wearer has walked that day, and thus the kilometers or miles walked or ran (distance=number of steps×step length). Some pedometers may also erroneously record movements other than walking, such as bending to tie one's shoes, or road bumps incurred while riding a vehicle, though the most advanced devices record fewer of these 'false steps'. Step counters are being integrated into an increasing number of portable consumer electronic devices such as music players and mobile phones.

BRIEF DESCRIPTION OF THE DRAWINGS

Particular embodiments in accordance with the invention will now be described, by way of example only, and with reference to the accompanying drawings:

FIGS. 3A-3C are plots illustrating waveforms generated during a sequence of steps by a 3-axis accelerometer in a wrist worn pedometer;

Figure 1:
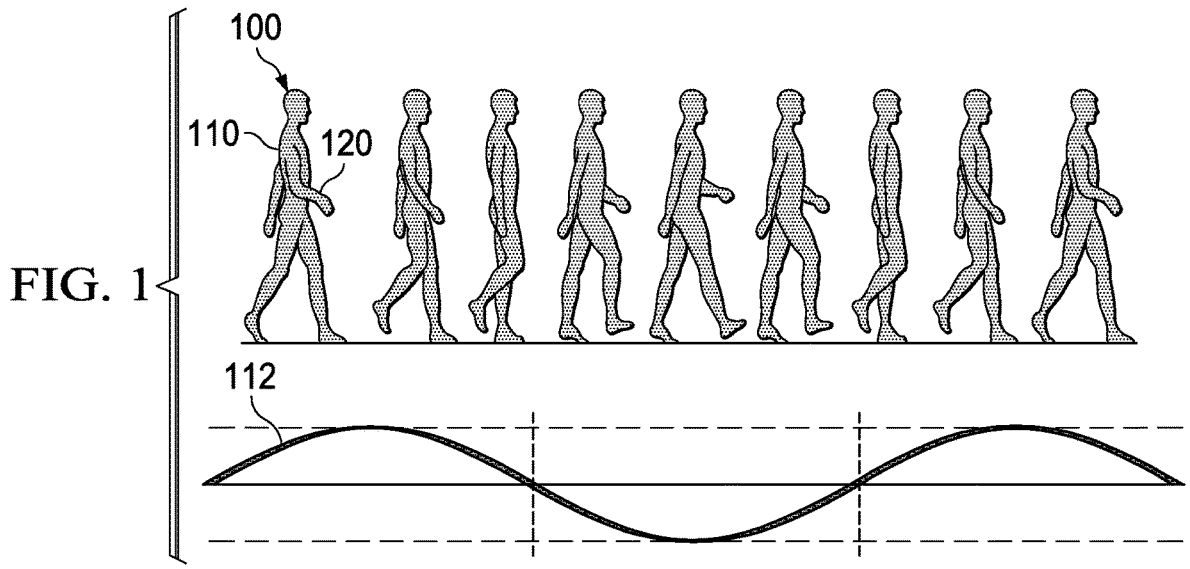
FIG. 1 is a diagram illustrating a typical step cycle of a person walking.

Other features of the present embodiments will be apparent from the accompanying drawings and from the detailed description that follows.

DETAILED DESCRIPTION OF EMBODIMENTS

Specific embodiments of the invention will now be described in detail with reference to the accompanying figures. Like elements in the various figures are denoted by like reference numerals for consistency. In the following detailed description of embodiments of the invention, numerous specific details are set forth in order to provide a more thorough understanding of the invention. However, it will be apparent to one of ordinary skill in the art that the invention may be practiced without these specific details. In other instances, well-known features have not been described in detail to avoid unnecessarily complicating the description.

Most pedometers on the market give accurate step counts when clipped to the user's belt or carried in the user's pocket but do not give an accurate step count when strapped to the wrist. Designing pedometers for the wrist-mounted case is a harder problem since the pedometer logic needs to account for the sway of the arm which generates acceleration comparable to that from an actual step. If the acceleration from the arm sway is not in sync with the acceleration from the step, inaccuracies may arise in the step count.

A pedometer suitable for robust pedestrian step detection using a 3-axis accelerometer will be described herein. Embodiments of the device and methods described herein work well for the wrist-mounted case as well as when belt-worn, clipped to a sports bra, or placed in a pocket, for example.

FIG. 1 is a diagram illustrating a typical step cycle of a person 100 walking. A pedometer clipped to the waist area 110 will be able to detect a generally sinusoidal motion waveform 112 using a simple accelerometer or other type of motion detecting device due to the periodic up and down vertical motion of the hips during walking or running. Likewise, a pedometer clipped to the chest area, such as on a sports bra or shirt pocket, will also be able to detect a generally sinusoidal motion waveform using a simple accelerometer or other type of motion detecting device due to the periodic up and down vertical motion of the torso during walking or running. Determining each step is then a fairly simple matter of detecting each peak of the sine wave and assuming each peak represents a step.

However, a pedometer worn on the wrist 120 will see a much more complex motion waveform due to the swinging motion of the arm in addition to the generally up and down motion of the torso and hips. As a result, prior art pedometers do not perform accurately when worn on the wrist.

Figure 2:
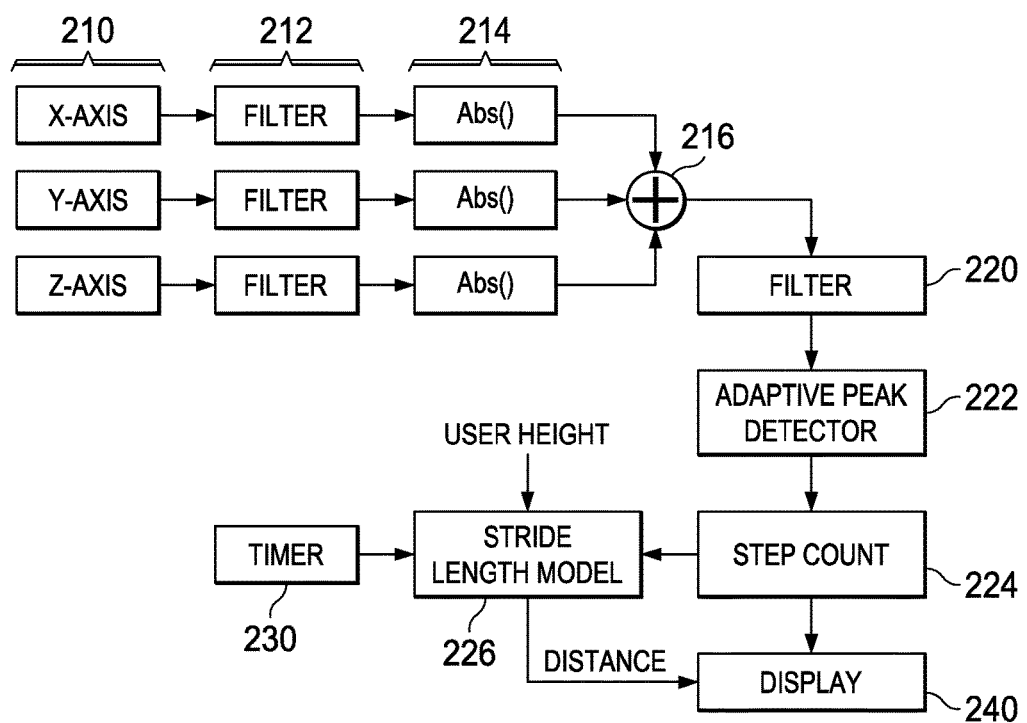
FIG. 2 is flow chart illustrating adaptive step detection for use in a pedometer.

FIG. 2 is flow chart illustrating adaptive step detection for use in a pedometer suitable for wearing on the wrist. A three axis accelerometer may be used in a pedometer for use on the wrist to provide motion information that is usable no matter which way the pedometer is oriented. In this example, data from each of the accelerometer's axes is collected into a circular type buffer 210 of length 800 msec long. A polynomial fit filter 212 of order three and frame length of approximately 400 msec is used to smooth each buffer to remove noise. In this embodiment, the window length of the filter is roughly 400 milliseconds and the order of the polynomial is roughly ⅛th the window length (in samples). In one particular implementation with sampling frequency of 62.5 Hz, the buffer length is 50 samples, the window length is 25 samples, and the order of the polynomial is three. Other embodiments may use different buffer lengths and/or filter lengths, or different types of buffers, such as first in first out (FIFO) type buffers.

The filtered signals are combined by summing 216 the absolute value 214 of each trio of samples from the three axes. The resulting signal is the combined acceleration from the three axes. The combined signal is smoothed using another polynomial fit filter 220. In this embodiment, the window length of filter 220 is approximately 200 milliseconds and the order of the polynomial is roughly ⅟₁₃th the window length (in samples). In one particular implementation with sampling frequency of 62.5 Hz, the window length is 13 and order of the polynomial is 1. Other embodiments may use different filter length.

In this embodiment, a low cost microprocessor is used to perform the filtering by executing instructions stored in a memory coupled to the microprocessor. The microprocessor first performs a digital polynomial filter algorithm on 50 samples in the x-axis buffer, then it performs a digital polynomial filter algorithm on 50 samples in the y-axis buffer, then it performs a digital polynomial filter algorithm on 50 samples in the z-axis buffer. Since it takes 25 samples to fill up the filter window, only 26 filtered samples are produced for each axis. The processor then determines the absolute value 214 of all of the filtered samples, and then adds 215 them together to form the combined 3-axis signal. The processor then applies filter 220 on the combined 3-axis signal. After completing this iteration, the processor then waits until the circular buffers 210 have received 26 more samples. Once the 26 new samples have been received, the new samples are appended to newest 24 samples from the previous iteration to form a buffer of 50 samples, the processor then repeats the filtering process on the 50 samples of data that are in the buffers 210. Again, since it takes 25 samples to fill up the filter window, only 26 filtered samples are produced for each axis. Thus, a simple processor may perform the four polynomial filter algorithms in an iterative manner. By using this window overlap method, the processor is able to discard the transient response of the filter, which enables the use of an FIR (finite impulse response) filter to achieve the polynomial fit filter based smoothing.

The difference between consecutive inflection points is computed in an adaptive peak detector 222 to obtain an estimate of the motion induced acceleration. Magnitude and time based thresholds are used to detect each step and thereby produce an accurate step count 224, as will be described in more detail below.

A stride length model 226 based approach is used to compute the distance traveled. The step frequency (number of steps per unit time) and user height is used to estimate the stride length and hence the distance traveled. Timer 230 is used to determine the number of steps per unit time. Alternatively, in some embodiments a user may perform a calibration process by walking a measured distance while the pedometer counts the number of steps it takes to walk or run the measured distance.

The resulting information may be displayed 240 on a display screen contained within the pedometer, and/or in some embodiments, a wireless link, such as Bluetooth, or wired link, such as USB (universal serial bus), may be used to transmit the data to another device such as a smart phone for displaying. The displayed data may include total number of steps since the last time the step count was reset, distance traveled, time of day, time to travel the distance, etc. A button or other user input mechanism may be included to allow the user to reset the count or select what information is being displayed.

Figure 3B:
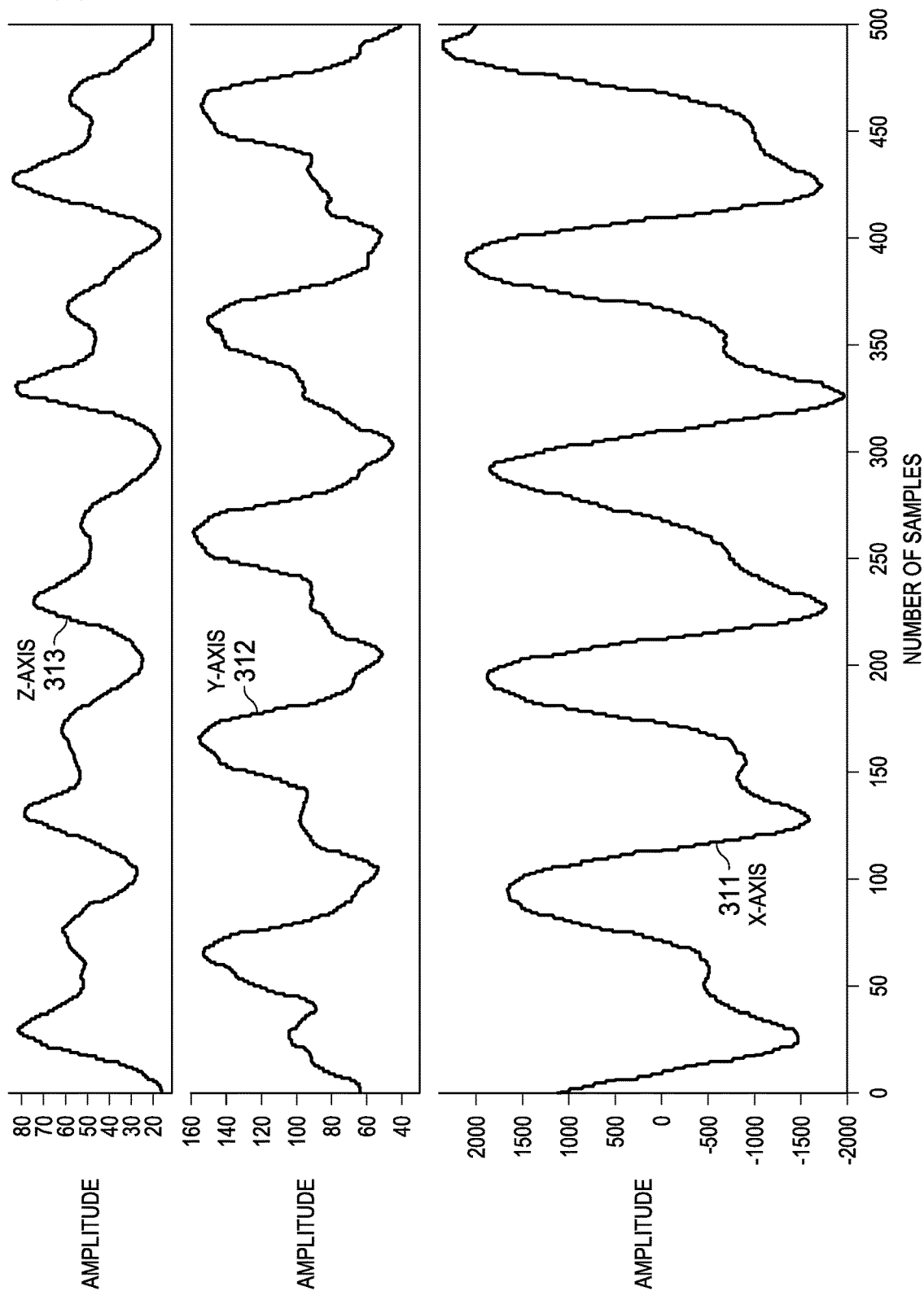

FIGS. 3A-3C are plots illustrating waveforms generated during a sequence of steps by a 3-axis accelerometer in a wrist worn pedometer. In FIG. 3A, waveforms are generated from an accelerometer that has three orthogonally oriented axes: x-axis 301, y-axis 302, and z-axis 303. In this embodiment, the sample rate is 62.5 Hz. Approximately ten actual steps occurred to generate the waveforms of FIG. 3A. Notice that in the x-axis 301 waveform, it would appear that only five peaks exist due to the interaction of arm swing and the movement of the torso in which the swing of an arm on the right side tends to cancel out the torso movement from the left leg, and vice versa. This is one reason why prior pedometers do not perform well when worn on the wrist. Notice that in the y-axis 302 and z-axis 303 plots, there is an indication that ten steps have occurred.

While the x-axis is dominant in FIG. 3A, since the orientation of a wrist worn pedometer may change, depending on how the user wears the device, face on top of wrist or on bottom of wrist, and how the user holds his/her arm while walking or running, the dominant axis may vary from time to time and from user to user. Thus, all three axes are used to produce a reliable result.

In this embodiment, fifty samples are collected in a circular buffer for each axis, as was mentioned above. This results in a frame in the buffer that is fifty samples wide that slides across the data samples, as illustrated by frame 310.

FIG. 3B illustrates the resultant waveforms 311-313 from polynomial fitted FIR filters 212, as described above.

FIG. 3C illustrates the combined waveform 320 formed by taking an absolute value 214 of each sample, adding 216 a sample from each of the tree axes to form a combined signal and then smoothing 220 the combined signal. Note, it is now apparent that the waveform represents approximately ten steps. However, since the amplitudes and duration of the peaks vary, an adaptive peak detector 222 is used to determine the most likely peaks that represent a true step.

Referring again to FIG. 3C, adaptive peak detector 222 analyzes the waveform to determine a region around each inflection point, such as indicated at 322, 323. It then determines if the amplitude of a region around an inflection point on a positive sloped portion of the waveform, such as at 330, exceeds a threshold value and if the time duration 331 of the positive sloping portion exceeds a threshold value. If both conditions are met, then the inflection point region is declared to represent a step and the step count is incremented. Then, a next negative inflection point region is located that has a magnitude 332 that exceeds a threshold value and a duration 333 that exceeds a threshold value. Once a negative inflection point region is identified that meets both criteria, then a search for the next positive inflection point commences.

In this manner, the actual value of a peak does not need to exceed a threshold value in order to be considered as a step indicator. However, a peak should have a long enough positive inflection point region so that it can be discriminated against noise and non-step motion.

Figure 4A:
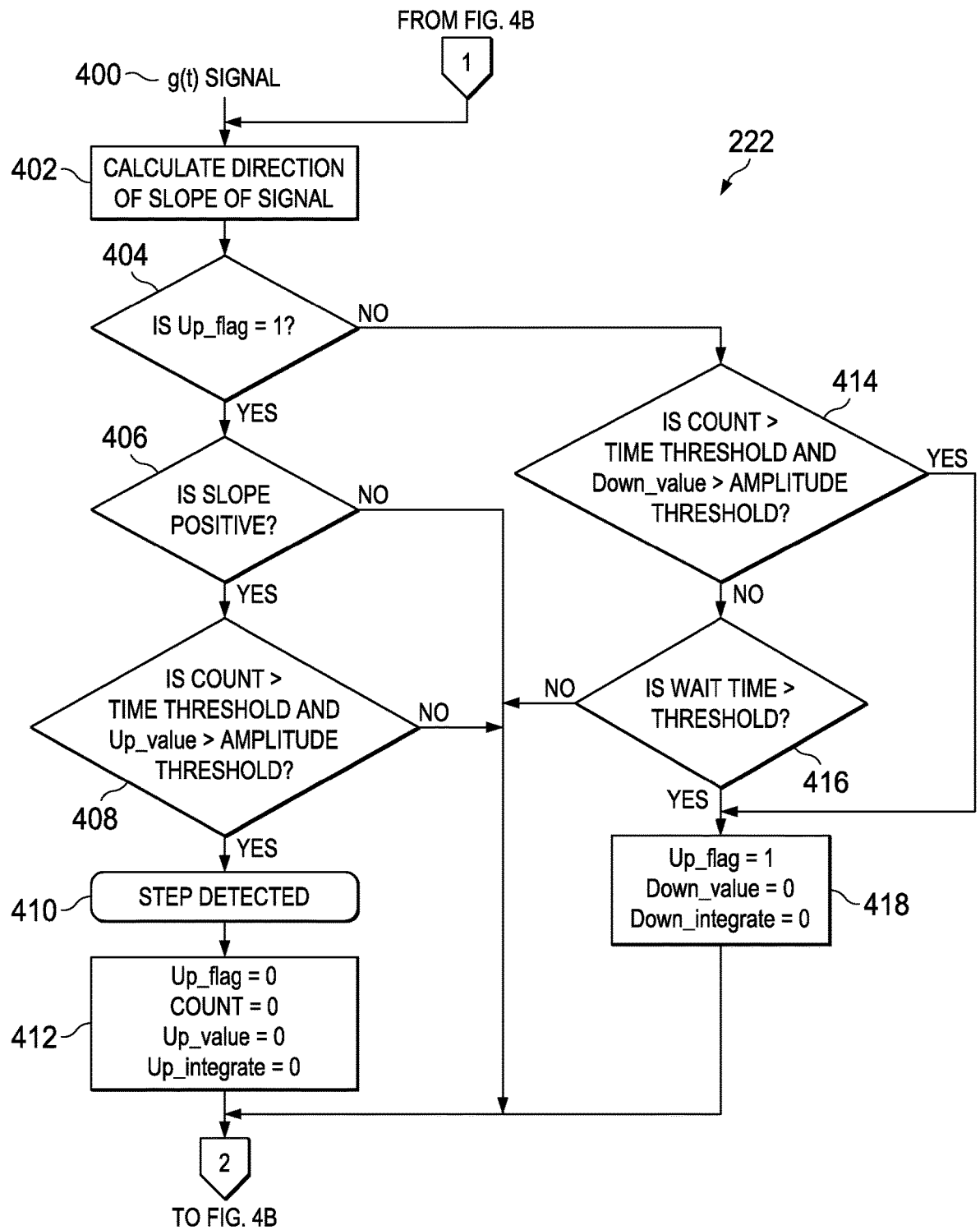
FIGS. 4A-4B together is a flow diagram illustrating operation of the adaptive peak detector.
Figure 4B:
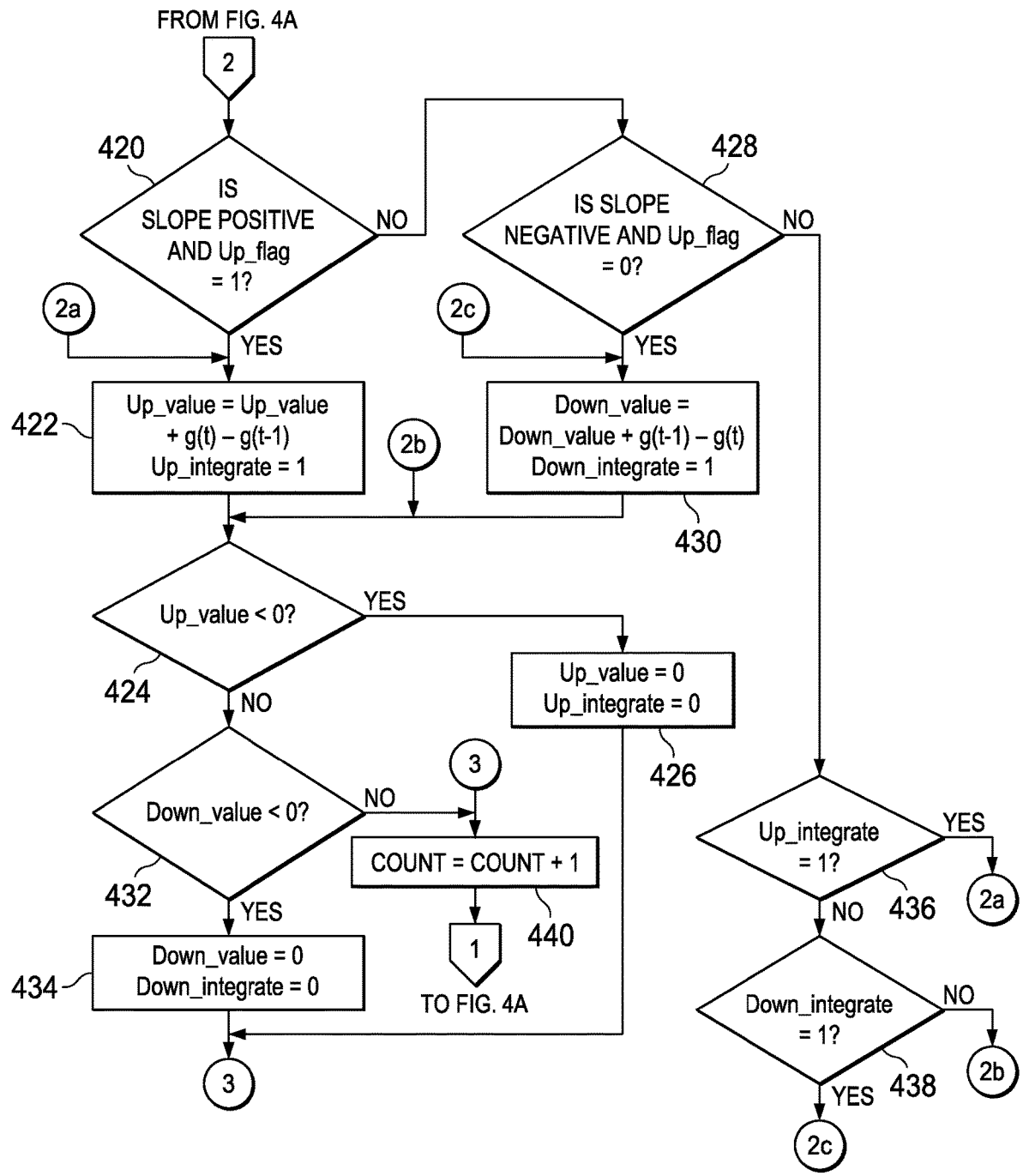

FIGS. 4A-4B together is a flow diagram illustrating operation of the adaptive peak detector 222 in more detail. Samples from the smoothed waveform are referred to as function g(t) 400 and are provided to the adaptive peak detector 222 sequentially. For each sample, a direction of the slope of the signal is calculated 402 by comparing the value of two samples.

After a positive sloping region that has an amplitude greater than an amplitude threshold and a sample count (duration) that is greater than a time threshold has been detected 408, then a step is declared 410 and a step counter is incremented. Then, the following parameters are set 412 to 0: up_flag, count, up_value, and up_integrate. This indicates that a positive inflection point region has been identified and that a search for a negative inflection region should now be performed. Similarly, after a negative region that has an amplitude greater than an amplitude threshold and a sample count (duration) that is greater than a time threshold has been detected 414, then the following parameters are set 418 as follows: up_flag=1, down_value=0, and down_integrate=0. Therefore, once a qualifying negative slope region is identified, the next qualifying positive slope region is searched for as indicated by up_flag=1.

Assume, for example, a qualifying negative region has been identified 418 and therefore the up_flag is one, meaning that a search for positive sloping region should now be performed. As each sample comes in 402, the flow will go from 404 to 406. If the slope is not positive, then a sequence of decisions 420, 428, 436, 438 will lead to up-value test 424. At this time, up-value is zero, so the sequence flows to down-value test 432 and then increments 440 a sample counter. The slope of the next sample is then evaluated 402 and the idle loop is repeated until a positive slope is detected 406.

Since the region amplitude is still zero, amplitude test 408 will go to up_flag test 420 and then to up_integration box 422, where the up_value is increased by the delta between the current sample and the prior sample. The sequence then flows through 424 since the up_value is greater than zero and through 432 to increment 440 the sample count. This loop repeats as long as the slope stays positive until the up_value exceeds the amplitude threshold 408, at which time another step is detected 410, and the up_flag is set to zero to indicate a search for a negative slope.

After detecting a step, the next several samples will likely have a positive slope. As each one comes in 402, the flow will go to the down_value test 414, since a search for a negative slope is now occurring. The flow will then fall through 420 because the up_flag is now zero, through 428, 436, 438, 424, 432, and then increments 440 the sample count.

This wait loop repeats until a negative slope sample is detected 428, at which point down integration box 430 is entered. The down count is then increased by the difference between the current sample and the prior sample. The count is then incremented 440 and this loop repeats until the down_value is greater than 414 the threshold value, at which point the negative slope search is complete 418 and the up_flag is again set to one.

At anytime during a positive region search with the up_flag set, if a "blip" in the waveform causes the integrated up_value to fall below a value of zero 424, then the up_integration is reset and a new search is started 426. Similarly, at anytime during a negative region search with the up_flag=zero, if a "blip" in the waveform causes the integrated down_value to fall below a value of zero 432, then the down_integration is reset and a new search is started 434. If a timeout 416 occurs during a negative slope region search without finding a qualifying negative region, then the up_flag will be set 418 and a search for a positive slope region will begin.

In some embodiments, the count time threshold and the amplitude threshold may be different for the positive slope search and for the negative slope search.

For 408 there are multiple combinations of time threshold and up acceleration amplitude threshold, for example: (176 ms, 3.48 m/sec-squared) or (240 msec, 2.72 m/sec-squared), (304 msec, 2.07 m/sec-squared) or (368 msec, 1.57 m/sec-squared) or (464 msec, 1.27 m/sec-squared). Similarly, for 414 there are multiple combinations of time threshold and down acceleration amplitude threshold, for example (80 msec, 0.12 m/sec-squared). For 416, an example wait time threshold is 944 msec. These are empirical values and other values may work as well.

In this manner, the combined 3-axis waveform data is examined to determine peaks using an adaptive algorithm that can detect peaks representative of steps even when motion of the wrist and motion of the torso combine to reduce the absolute value of various peaks.

Table 1 illustrates tests results for a representative older pedometer device and a new device that embodies the techniques described herein. Both devices were strapped at the same time to the wrist of various subjects. As can be seen in Table 1, the new device more nearly counted that actual number of steps that were taken by the various test subjects. Table 2 illustrates a series of different tests performed using the same subject with both the old and the new devices strapped to his/her wrist. Again, the error in step counts from the new device was lower than from the old device. Table 3 illustrates a series of tests performed on a treadmill in which the old device was worn on the belt of the test subject while the new device was strapped to the wrist of the test subject. In this case, the new device on the wrist demonstrated a performance that was essentially as accurate as the old device on the waist.

TABLE 1

Comparison between a prior pedometer (Old) and an improved pedometer (New) for multiple test subjects, wrist mounted, walking, sampling frequency = 62.5 Hz

| Subject | True Steps | Old | New |
| --- | --- | --- | --- |
| Subject 1 a | 154 | 8 | 97 |
| Subject 2 | 155 | 89 | 157 |
| Subject 3 | 171 | 149 | 169 |
| Subject 4 | 147 | 129 | 145 |
| Subject 5 | 177 | 92 | 172 |
| Subject 6 | 153 | 150 | 151 |
| Subject 7 | 153 | 53 | 152 |
| Subject 1 b | 154 | 45 | 95 |

TABLE 2

Multiple scenarios, same test subject, sampling freq = 62.5 Hz

| ID | True Steps | Old | New | Old Error | New Error | Comments |
| --- | --- | --- | --- | --- | --- | --- |
| it01 | 100 | 99 | 100 | −1 | 0 | hip clipped, brisk walk |
| it02 | 100 | 99 | 101 | −1 | 1 | hip clipped, light jog |
| it03 | 100 | 100 | 99 | 0 | −1 | wrist mounted, normal walk, low swing |
| it05 | 100 | 16 | 69 | −84 | −31 | wrist mounted, brisk walk, brisk swing |
| it06 | 100 | 18 | 100 | −82 | 0 | wrist mounted, brisk walk, normal swing |
| it07 | 100 | 99 | 102 | −1 | 2 | wrist mounted, bent elbow, low swing |
| it08 | 100 | 101 | 101 | 1 | 1 | wrist mounted, bent elbow, jog |
| it09 | 100 | 95 | 103 | −5 | 3 | wrist mounted, slow walk, no swing |
| it10 | 100 | 78 | 100 | −22 | 0 | wrist mounted, slow walk, normal swing |
| it11 | 100 | 86 | 98 | −14 | −2 | wrist mounted, medium walk, normal swing |
| it12 | 100 | 99 | 96 | −1 | −4 | wrist mounted, normal walk, low swing |
| it13 | 100 | 56 | 74 | −44 | −26 | wrist mounted, waddle, medium swing |
| it14 | 100 | 176 | 100 | 76 | 0 | wrist mounted, waddle, no swing |

TABLE 3

Treadmill test, comparison with a belt worn pedometer

| Test Condition | True Steps | Old on belt | New on wrist |
|---|---|---|---|
| 2.5 mph walking (hand on side, normal swing) | 110 | 111 | 112 |
| 3 mph walking (hands on side, normal swing) | 125 | 123 | 124 |
| 3 mph walking (elbow bent, normal swing) | 100 | 101 | 101 |
| 4.5 mph walking (hands on the side, normal swing) | 100 | 100 | 107 |
| 4.5 mph walking (elbow bent, normal swing) | 100 | 101 | 97 |
| 5.5 mph running (elbow bent, normal swing) | 100 | 101 | 99 |
| 6.5 mph running (elbow bent, normal swing) | 100 | 101 | 99 |
| 10 mph running (elbow bent, normal swing) | 125 | 123 | 116 |

Figure 5:
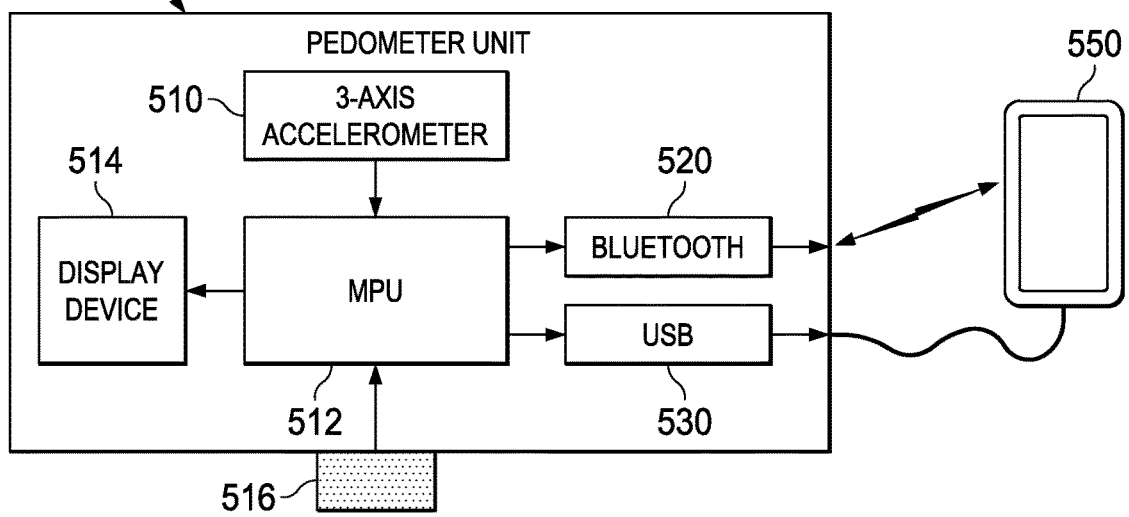
FIG. 5 is a block diagram of an exemplary pedometer.

FIG. 5 is a block diagram of an exemplary pedometer 500. Three axis accelerometer 510 may be coupled to microcontroller 512 using an input interface provided by microcontroller 512. Microcontroller 512 may be a MSP430 device, available from Texas Instruments Inc, for example. Microcontroller 512 includes memory that may be configured to use as the circular buffers and read only memory that may be loaded with software instructions that perform the filtering and adaptive peak detection described herein. A display device 514 may be coupled to microcontroller 512 and used to display step count, distance covered, elapsed time, time of day, etc. Push button 516 may be coupled to microcontroller 512 and used to select what information is to be displayed, for example by sequencing through a list of display options.

In some embodiments, a transceiver 520, such as a Bluetooth transceiver, may be coupled to microcontroller 512 and used to transmit display data to another device 550, such as a smart phone or other personal digital assistant, a laptop computer, a desktop computer, etc. In this case, display 514 may be omitted from pedometer 500.

In some embodiments, a USB (universal serial bus) transceiver 530 may be coupled to microcontroller 512 and used to transmit display data to another device 550, such as a smart phone or other personal digital assistant, a laptop computer or a desktop computer, for example. In this case, display 514 may be omitted from pedometer 500.

In another embodiment, 3-axis accelerometer 510 may be located within device 550, which may be a smart phone, for example. Mobile phone 550 is representative of any of several smart phones that are available from a variety of vendors. A smart phone typically includes processing hardware and capabilities that may be used to perform the filtering and detection algorithms described herein. Application software, also referred to as an "app," may be downloaded into the phone using the normal app download process for that smart phone. The app may be configured to perform the filtering, adaptive peak detection, and display features described in more detail above by executing software instructions stored in memory that is accessible by a processor that is included within smart phone 550. In this manner, the smart phone may provide the function of a pedometer.

Figure 6:
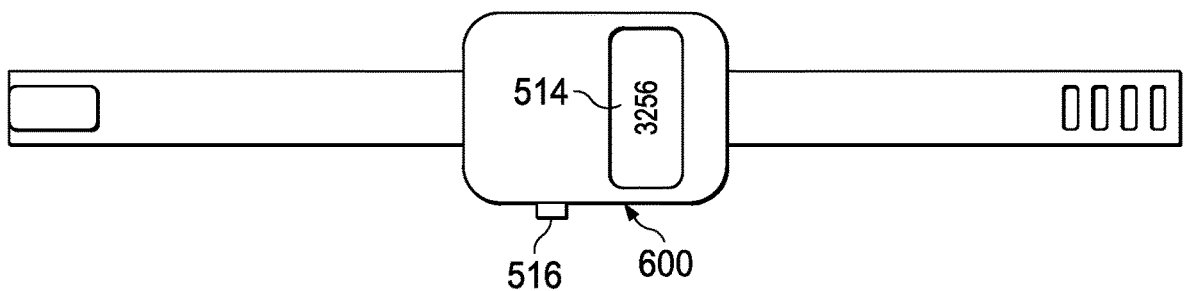
FIG. 6 illustrates an embodiment of a wrist pedometer.

FIG. 6 illustrates an embodiment of a wrist pedometer 600. Wrist pedometer 600 may include a 3-axis accelerometer that may be coupled to a microcontroller using an input interface provided by microcontroller. The microcontroller may be a MSP430 device, available from Texas Instruments Inc, for example. The microcontroller includes memory that may be configured to use as the circular buffers and read only memory that may be loaded with software instructions that perform the filtering and adaptive peak detection described herein. A display device may be coupled to the microcontroller and used to display step count, distance covered, elapsed time, time of day, etc. A push button may be coupled to the microcontroller and used to select what information is to be displayed, for example by sequencing through a list of display options.

In some embodiments, a Bluetooth transceiver may be coupled to the microcontroller and used to transmit display data to another device, such as a smart phone or other personal digital assistant. In this case, a display may be omitted from pedometer 600.

Other Embodiments

While the invention has been described with reference to illustrative embodiments, this description is not intended to be construed in a limiting sense. Various other embodiments of the invention will be apparent to persons skilled in the art upon reference to this description. For example, the pedometer may be packaged in various manners now known or later developed that will provide protection and ease of use. For example, the package may be waterproof and rugged so that the device may be permanently attached to a shirt or sports bra and survive normal use and cleaning processes.

The pedometer may be battery powered, or it may be packaged with an energy scavenging unit that derives power from motion of the test subject, solar energy, etc.

While a wired USB link or a wireless blue tooth link have been described, other embodiments may use any sort of known or later developed wired (metallic or optical) or wireless interconnect protocol that supports the necessary transfer rate to support transmission of display data.

While a smart phone was described herein for providing a display option, other types of mobile consumer devices may be used to provide a display option and/or also provide filtering and adaptive peak detection functions described herein, such as a tablet computer, a personal digital assistant, etc. In general, as used herein, a consumer device is a general purpose device that may be used by a consumer for other tasks in additional to providing pedometer display.

Embodiments of the filters and methods described herein may be provided on any of several types of digital systems: digital signal processors (DSPs), general purpose programmable processors, application specific circuits, or systems on a chip (SoC) such as combinations of a DSP and a reduced instruction set (RISC) processor together with various specialized accelerators. An SoC may contain one or more megacells which each include custom designed functional circuits combined with pre-designed functional circuits provided by a design library.

The techniques described in this disclosure may be implemented in hardware, software, firmware, or any combination thereof. If implemented in software, the software may be executed in one or more processors, such as a microprocessor, application specific integrated circuit (ASIC), field programmable gate array (FPGA), or digital signal processor (DSP). The software that executes the techniques may be initially stored in a computer-readable medium such as compact disc (CD), a diskette, a tape, a file, memory, or any other computer readable storage device and loaded and executed in the processor. In some cases, the software may also be sold in a computer program product, which includes the computer-readable medium and packaging materials for the computer-readable medium. In some cases, the software instructions may be distributed via removable computer readable media (e.g., floppy disk, optical disk, flash memory, USB key), via a transmission path from computer readable media on another digital system, etc.

Certain terms are used throughout the description and the claims to refer to particular system components. As one skilled in the art will appreciate, components in digital systems may be referred to by different names and/or may be combined in ways not shown herein without departing from the described functionality. This document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" and derivatives thereof are intended to mean an indirect, direct, optical, and/or wireless electrical connection. Thus, if a first device couples to a second device, that connection may be through a direct electrical connection, through an indirect electrical connection via other devices and connections, through an optical electrical connection, and/or through a wireless electrical connection.

Although method steps may be presented and described herein in a sequential fashion, one or more of the steps shown and described may be omitted, repeated, performed concurrently, and/or performed in a different order than the order shown in the figures and/or described herein. Accordingly, embodiments of the invention should not be considered limited to the specific ordering of steps shown in the figures and/or described herein.

It is therefore contemplated that the appended claims will cover any such modifications of the embodiments as fall within the true scope and spirit of the invention.

What is claimed is:

1. A device comprising:
    a three-axis accelerometer; and
    a processor coupled to the three-axis accelerometer and configured to:
        receive three-axis data, from the three-axis accelerometer, that includes data for each of a plurality of axes;
        perform a first polynomial filter operation on the data for each of the axes of the three-axis data to generate filtered samples for each of the axes;
        combine the filtered sample from each of the axes of the three-axis data into a combined data stream;
        perform a second polynomial filter operation on the combined data stream to generate a filtered combined data stream;
        identify positive slope regions, in the filtered combined data stream, that have a positive slope and a magnitude that exceeds a positive amplitude threshold value;
        identify negative slope regions, in the filtered combined data stream, that have a negative slope and a magnitude that exceeds a negative amplitude threshold value; and
        identify at least one occurrence of an identified positive slope region that is separated by an identified negative slope region.

2. The device of claim 1, wherein the processor is further configured to store the three-axis data in three circular buffers, and to iteratively perform a finite impulse response (FIR) polynomial filter operation on the three-axis data in each of the three circular buffers.

3. The device of claim 1, further comprising a transmitter coupled to the processor configured to transmit step information to a remote display device.

4. The device of claim 1, wherein the positive amplitude threshold value is different than the negative amplitude threshold value.

5. The device of claim 1, wherein the device includes a display, and wherein the processor is further configured to display the number of counted steps on the display.

6. A method comprising:
    receiving, with one or more processors, three-axis data from the three-axis accelerometer, the three-axis data including data for each of a plurality of axes;
    performing, with the one or more processors, a first polynomial filter operation on the data for each of the axes of the three-axis data to generate filtered samples for each of the axes;
    combine the filtered sample from each of the axes of the three-axis data into a combined data stream;
    performing, with the one or more processors, a second polynomial filter operation on the combined data stream to generate a filtered combined data stream;
    identifying, with the one or more processors, positive slope regions, in the filtered combined data stream, that have a positive slope and a magnitude that exceeds a positive amplitude threshold value;
    identifying, with the one or more processors, negative slope regions, in the filtered combined data stream, that have a negative slope and a magnitude that exceeds a negative amplitude threshold value; and
    incrementing, with the one or more processors, a step count for at least one occurrence of an identified positive slope region that is separated by an identified negative slope region as a step.

7. The method of claim 6, wherein the three-axis data is received into three circular buffers, and wherein performing the first polynomial filter operation includes filtering the three-axis data in an iterative manner using a finite impulse response (FIR) polynomial filter operation on each axis of data in the three circular buffers.

8. The method of claim 6, wherein the positive amplitude threshold value is different than the negative amplitude threshold value.

9. A device comprising:
    a three-axis accelerometer; and
    a processor coupled to the three-axis accelerometer and configured to:
        receive three-axis data, from the three-axis accelerometer, that includes data for each of a plurality of axes;
        perform a first polynomial filter operation on the data for each of the axes of the three-axis data to generate filtered samples for each of the axes;
        combine the filtered sample from each of the axes of the three-axis data into a combined data stream;
        perform a second polynomial filter operation on the combined data stream to generate a filtered combined data stream; and
        increment a step count based on the filtered combined data stream.

10. The device of claim 9, wherein the processor is further configured to filter the three-axis data in an iterative manner using a finite impulse response (FIR) polynomial filter operation on each axis of data in the three-axis data.

11. The device of claim 9, wherein the device includes a display, and wherein the processor is further configured to display the number of counted steps on the display.

* * * * *